United States Patent [19]

Schröder et al.

[11] 4,117,135

[45] Sep. 26, 1978

[54] NOVEL 5,6,7,8-TETRAHYDRO-5-QUINOLINES AND THEIR USE AS ANTI-INFLAMMATORY AGENTS

[75] Inventors: Eberhard Schröder; Henning Koch, both of Berlin, Germany

[73] Assignee: Schering, A.G., West Berlin

[21] Appl. No.: 620,777

[22] Filed: Oct. 8, 1975

[30] Foreign Application Priority Data

Oct. 11, 1974 [DE] Fed. Rep. of Germany ....... 2449030

[51] Int. Cl.² ................. C07D 215/16; A61K 31/47; C07D 215/18; C07D 215/20
[52] U.S. Cl. ............................ 424/258; 260/283 CN; 260/283 R; 260/280 CE; 260/289 H; 260/294.9; 260/295 F; 260/295 K; 260/296 B; 424/263
[58] Field of Search ........ 260/283 CN, 283 T, 287 T, 260/288 CE, 289 H; 424/258

[56] References Cited

U.S. PATENT DOCUMENTS

| 3,322,770 | 5/1967 | D'Alessandro et al. ......... 260/283 T |
| 3,531,493 | 9/1970 | Gittos et al. ..................... 260/287 K |
| 3,998,831 | 12/1976 | Curran ............................ 260/289 H |
| 4,011,225 | 3/1977 | Curran et al. ................. 260/283 CN |

OTHER PUBLICATIONS

Juby et al.; *J. Med. Chem.*, vol. 12, pp. 396–401 (1969).
Juby et al.; *J. Med. Chem.*, vol. 11, pp. 111–117, (1968).
Buchanan et al., *J. Med. Chem.* vol. 12, pp. 1001–1006, (1969).
Morrison et al., *Organic Chemistry* 2nd Edition, pp. 589–591, (1969).
Seibert et al.; *Chem. Abst.* vol. 41: 2054a (1947).
Protiva et al.; *Chem. Abst.* vol. 45: 9522a (1951).
Narda et al.; *Chem. Abst.* vol. 47: 11140b (1952).

*Primary Examiner*—Donald G. Daus
*Assistant Examiner*—M. Vaughn
*Attorney, Agent, or Firm*—Millen & White

[57] ABSTRACT

Pyridine derivatives of the formula

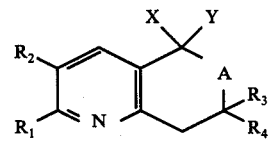

wherein $R_1$ is an alkyl, aliphatic, a cycloalkyl, or a substituted or unsubstituted hydrocarbon aryl and the substituent is halogen, alkoxy or methylenedioxy; $R_2$ is H or Cl; X is CN, 5-tetrazolyl, or COOH or a carboxylic acid derivative; Y is H, OH, $OCOR_7$, $NH_2$, $NHCOR_8$, $R_9$, COOH or $COOR_{10}$ and $R_7$, $R_8$, $R_9$ and $R_{10}$ are alkyl groups of 1-10 carbon atoms; A is methylene or a carbon-to-carbon bond; and $R_3$ and $R_4$ are each H or alkyl groups of 1-4 carbon atoms, are useful as anti-inflammatory agents.

31 Claims, No Drawings

NOVEL 5,6,7,8-TETRAHYDRO-5-QUINOLINES AND THEIR USE AS ANTI-INFLAMMATORY AGENTS

BACKGROUND OF THE INVENTION

This invention relates to novel, pharmacologically effective pyridine derivatives, a process for the preparation thereof, pharmaceutical preparations containing these compounds and a method of treating inflammation therewith.

SUMMARY OF THE INVENTION

The compounds of this invention are novel pyridine derivatives of the formula

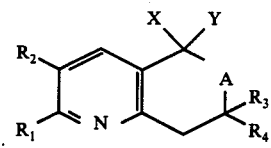

wherein $R_1$ is an alkyl of 1–10 carbon atoms, cycloalkyl of 3–10 carbon atoms, hydrocarbon aryl of 6–10 carbon atoms or the aryl substituted by at least one of halogen, alkoxy or methylenedioxy; $R_2$ is H or Cl; X is CN, 5-tetrazolyl, $CONH_2$, CONHOH or COOH or a physiologically acceptable salt thereof with a base or a physiologically acceptable ester thereof, or a physiologically acceptable substituted or unsubstituted hydrocarbon group; Y is H, OH, an alkanoyloxy of 1–6 carbon atoms, an alkanoyl amino of 1–6 carbon atoms in the alkanoyl group, alkyl of 1–10 carbon atoms, carboxy or alkoxycarbonyl of 1–6 carbon atoms in the alkoxy group; A is methylene or a carbon-to-carbon bond; and $R_3$ and $R_4$ are each H or alkyl groups of 1–4 carbon atoms.

DETAILED DISCUSSION

The pyridine derivatives of this invention include both the racemates and their optically active antipodes. Racemates can be mechanically or chemically separated into their optical antipodes by known methods, preferably by reaction with optically-active separating agents. For example, a racemate of general Formula I which contains a carboxylic acid group, can be reacted with an optically-active base and the diastereomeric mixtures obtained separated by fractional crystallization or by manuel selection.

In the above formula, —A— can be represented by —$(CH_2)_n$— wherein $n$ is 0 or 1.

Thus, the compounds of this invention are tetrahydroquinoline derivatives substituted in at least the 2- and 5-positions or 6,7-dihydro-5H-cyclopenta[b]pyridine derivatives substituted in at least the 2- and 5-positions.

The substituent $R_1$ at the 2-position of the pyridine ring is a hydrocarbon group of 1–10 carbon atoms, e.g., alkyl of 1–10 carbon atoms, cycloalkyl of 3–10 carbon atoms, hydrocarbon aryl of 6–10 carbon atoms or the aryl substituted by at least one of halogen, alkoxy or methylenedioxy.

Preferred substituents at the 2-position include straight-chain and branched-chain alkyl groups of 1–6 carbon atoms, cycloalkyl groups of 5–7 carbon atoms, and phenyl groups which can be substituted by halogen atoms, such as fluorine or chlorine; by trifluoromethyl groups; by methylenedioxy groups; by lower alkoxy groups, such as the methoxy or ethoxy group, or by lower alkyl groups of 1–4 carbon atoms, including the methyl group, the ethyl group, the propyl group, the isopropyl group, the butyl group, and the tert.-butyl group. Typical examples of preferred substituents represented by $R_1$ are; methyl, ethyl, propyl, isopropyl, butyl, isobutyl, pentyl, isopentyl, and hexyl, which are exemplary of alkyl of 1–6 carbon atoms; cyclopentyl, cyclohexyl and cycloheptyl, which exemplify cycloalkyls of 5–7 carbon atoms; phenyl, o-tolyl, m-tolyl, p-tolyl, p-cumene, and p-tert.-butylphenyl, which exemplify aryl hydrocarbon aryl of 6–10 carbon atoms; o-methoxyphenyl, m-methoxyphenyl, p-methoxyphenyl, o-fluorophenyl, m-fluorophenyl, p-fluorophenyl, o-chlorophenyl, m-chlorophenyl, p-chlorophenyl, o-trifluoromethylphenyl, m-trifluoromethylphenyl, p-trifluoromethylphenyl, o-bromophenyl, m-bromophenyl, p-bromophenyl, 2,5-dichlorophenyl, 3,4-dichlorophenyl, 2,4-dichlorophenyl, 2-chloro-3-tolyl, 3-chloro-2-tolyl, 3-chloro-4-tolyl, 3,4-dimethoxyphenyl, and 3,4-methylenedioxyphenyl, which exemplify substituted aryl.

One of the substituents at the 5-position of the tetrahydroquinoline or cyclopenta[b]pyridine derivatives of this invention is represented by X; the other 5-substituent by Y. The X substituent is 5-tetrazolyl, cyano, carbomoyl, hydroxamic acid, carboxy or an acceptable salt thereof with a base or a physiologically acceptable ester thereof or a physiologically acceptable amide thereof.

Examples of physiologically acceptable salts are the alkali or alkaline earth metal salts, including the sodium or calcium salt, as well as the ammonium salt, and the methylglucamine salt.

Physiologically acceptable alcohols suitable for esterifying the carboxyl group include substituted or unsubstituted hydrocarbon groups including straight-chain, branched or cyclic, saturated or unsaturated hydrocarbon residues which can optionally be interrupted by an oxygen atom or a nitrogen atom, or substituted with hydroxy groups, amino groups, or carboxyl groups, such as, for instance, alkanols, alkenols, alkinols, cycloalkanols, cycloalkenols, cycloalkylalkanols, phenylalkanols, phenylalkenols, alkanediols, hydroxycarboxylic acids, aminoalkanols, or alkylaminoalkanols and dialkylaminoalkanols of 1–4 carbon atoms in the alkyl residue.

Alcohols suitable for the esterification of the carboxyl group include both substituted and unsubstituted alkanols, for example, methyl, carboxymethyl, ethyl, 2-hydroxyethyl, 2-methoxyethyl, 2-aminoethyl, 2-dimethylaminoethyl, 2-carboxyethyl, propyl, allyl, cyclopropylmethyl, isopropyl, 3-hydroxypropyl, propinyl, 3-aminopropyl, butyl, sec.-butyl, tert.-butyl, 2-butyl, cyclobutyl, pentyl, isopentyl, tert.-pentyl, 2-methylbutyl, cycloalkanols and cycloalkylalkanols, cyclopentyl, hexyl, cyclohexyl, cyclo-2-enyl, cyclopentylmethyl, heptyl, benzyl, 2-phenylethyl, octyl, bornyl, isobornyl, menthyl, nonyl, decyl, 3-phenylpropyl, 3-phenylprop-2-enyl, undecyl, and dodecyl. Also suitable for esterification are those alcohols leading to labile esters, i.e. esters which can be split under physiological conditions, such as 5-hydroxyindan, acyloxymethanols, especially acetoxymethanol, pivaloyloxymethoxymethanol, 5-indanyloxycarbonylmethanol, glycolic acid, dialkylaminoalkanols, especially dimethylaminopropanol, as well as hydroxyphthalide.

Preferred alcohols are alkanols of 1 to 8 carbon atoms, for example methanol, ethanol, propanol, isopropanol, butanol, tert butanol, 1-pentanol, 1-hexanol or 1-octanol.

Physiologically acceptable amines with which the carboxyl group can be amidated include alkylamines, dialkylamines or heterocyclic amines.

Preferred as the physiologically acceptable amines with which the carboxyl group can be amidated are alkylamines, dialkylamines, alkanolamines, dialkanolamines of 1–6 carbon atoms in the alkyl or alkanol residue, or five- or six-membered N-heterocycles. Examples of preferred amines are: methylamine, ethylamine, isopropylamine, ethanolamine, dimethylamine, diethylamine, diethanolamine, pyrrolidine, piperidine, morpholine, or N-methylpiperazine.

The substituent represented by Y at the 5-position of the compounds of this invention is selected from hydrogen, hydroxy, acyloxy, amino, acylamido, alkyl, carboxyl, or carbolkoxy.

Preferred acyloxy and acylamino groups are those derived from n-alkanoic acids of 1–6 carbon atoms, acids including formic acid, acetic acid, propionic acid, butyric acid, valeric acid or caproic acid.

When Y is carbalkoxy, the preferred alkyls have 1–6 carbon atoms, such as methyl, ethyl, or butyl.

When Y is alkyl, the preferred groups have 1–4 carbon atoms, such as methyl or ethyl.

Examples of classes of compounds within the scope of Formula I are:

(a) 2-phenyl-5,6,7,8-tetrahydro-5-quinolinecarboxylic acid and related derivatives of the carboxyl group, including those in which X is CN, COOH, carbalkoxy of 1–12 carbon atoms in the alkoxy, carbamoyl, N-alkylcarbamoyl, hydroxamic acid or 5tetrazolyl. Of the carbalkoxy compounds, the carbomethoxy and carbethoxy compounds are especially preferred. Of N-alkylcarbamoyl substituents, an alkyl of 1–4 carbon atoms is preferred.

(b) 2-phenyl-5,6,7,8-tetrahydroquinoline carboxylic acid derivatives substituted at the 5-position by a second substituent Y, which is OH, acyloxy of 1–10 carbon atoms in the acyl, amino, acylamino of 1–10 carbon atoms in the acyl group, or alkyl of 1–10 carbon atoms. Of the foregoing, preferred acyloxy groups include acetoxy and a preferred acylamino group is N-acetylamino.

(c) those wherein X is cyano, substituted at the 2-position by an aryl hydrocarbon or an alkyl, i.e., compounds of Formula I wherein $R_1$ is alkyl of 1–10 carbon atoms, aryl hydrocarbon of 7–10 carbon atoms or aryl hydrocarbon of 6–10 carbon atoms substituted by at least one of halogen alkoxy or methylenedioxy; $R_2$ is H or Cl; $H_3$, $R_4$ and Y each are H; A is methylene and X is cyano. Also preferred are the related acids, in which X is COOH.

(d) tetrahydroquinoline-5-carboxylic acids substituted at the 7-position by two methyl groups and at the 2-position by a hydrocarbon aryl of 6–10 carbon atoms, i.e., compounds of Formula I in which $R_1$ is hydrocarbon aryl of 6–10 carbon atoms, $R_2$ and Y are H, $R_3$ and $R_4$ each are methyl, A is methylene and X is CN or COOH.

Also preferred for the practice of this invention are dihydro-5-H-cyclopenta[b]pyridine-5-carboxylic acid derivatives of Formula I, wherein $R_1$ is a hydrocarbon aryl of 6–10 carbon atoms or cycloalkyl of 3–10 carbon atoms; $R_2$ is H or Cl; $R_4$ $R_3$, $R_4$ and Y each are H; A is a carbon-to-carbon bond and X is CN, COOH, carbalkoxy of 1–10 carbon atoms in the alkoxy, carbamoyl, N-alkylcarbamoyl of 1–10 carbon atoms in the alkyl, hydroxamic acid or 5-tetrazolyl. Of the carbalkoxy groups, carbomethoxy and carbethoxy are especially preferred.

The following are illustrative of compounds of this invention:

2-phenyl-5,6,7,8-tetrahydro-5-quinolinecarboxylic acid
2-phenyl-3-chloro-5,6,7,8-tetrahydro-5-quinolinecarboxylic acid
2-(2-chlorophenyl)-5,6,7,8-tetrahydro-5-quinolinecarboxylic acid
2-(3-chlorophenyl)-5,6,7,8-tetrahydro-5-quinolinecarboxylic acid
2-(4-chlorophenyl)-5,6,7,8-tetrahydro-5-quinolinecarboxylic acid
2-(4-chlorophenyl)-3-chloro-5,6,7,8-tetrahydro-5-quinolinecarboxylic acid
2-(2-fluorophenyl)-5,6,7,8-tetrahydro-5-quinolinecarboxylic acid
2-(3-fluorophenyl)-5,6,7,8-tetrahydro-5-quinolinecarboxylic acid
2-(4-chlorophenyl)-3-chloro-5,6,7,8-tetrahydro-5-quinolinecarboxylic acid
2-(3-bromophenyl)-5,6,7,8-tetrahydro-5-quinolinecarboxylic acid
2-(2,5-dichlorophenyl)-5,6,7,8-tetrahydro-5-quinolinecarboxylic acid
2-(3,4-dichlorophenyl)-5,6,7,8-tetrahydro-5-quinolinecarboxylic acid
2-(3,4-dichlorophenyl)-3-chloro-5,6,7,8-tetrahydro-5-quinoline carboxylic acid
2-(2,4-dichlorophenyl)-5,6,7,8-tetrahydro-5-quinolinecarboxylic acid
2-(2,4-dichlorophenyl)-3-chloro-5,6,7,8-tetrahydro-5-quinolinecarboxylic acid
2-(2-trifluoromethylphenyl)-5,6,7,8-tetrahydro-5-quinolinecarboxylic acid
2-(3-trifluoromethylphenyl)-5,6,7,8-tetrahydro-5-quinolinecarboxylic acid
2-(4-trifluoromethylphenyl)-5,6,7,8-tetrahydro-5-quinolinecarboxylic acid
2-(4-trifluoromethylphenyl)-3-chloro-5,6,7,8-tetrahydro-5-quinolinecarboxylic acid
2-(3-tolyl)-5,6,7,8-tetrahydro-5-quinolinecarboxylic acid
2-(4-tolyl)-5,6,7,8-tetrahydro-5-quinolinecarboxylic acid
2-(3-chloro-4-tolyl)-5,6,7,8-tetrahydro-5-quinolinecarboxylic acid
2-(2-chloro-3-tolyl)-5,6,7,8-tetrahydro-5-quinolinecarboxylic acid
2-(3-chloro-2-tolyl)-5,6,7,8-tetrahydro-5-quinolinecarboxylic acid
2-(2-methoxyphenyl)-5,6,7,8-tetrahydro-5-quinolinecarboxylic acid
2-(3-methoxyphenyl)-5,6,7,8-tetrahydro-5-quinolinecarboxylic acid
2-(4(methoxyphenyl)-5,6,7,8-tetrahydro-5-quinolinecarboxylic acid
2-(4-methoxyphenyl)-3-chloro-5,6,7,8-tetrahydro-5-quinolinecarboxylic acid
2-(3,4-dimethoxyphenyl)-5,6,7,8-tetrahydro-5-quinolinecarboxylic acid
2-(3,4-dimethoxyphenyl)-3-chloro-5,6,7,8-tetrahydro-5-quinolinecarboxylic acid
2-(3,4-methylenedioxyphenyl)-5,6,7,8-tetrahydro-5-quinolinecarboxylic acid (3,4-methylenedioxyphenyl)-3-chloro-5,6,7,8-tetrahydro-5-quinolinecarboxylic acid
2-cyclopentyl-5,6,7,8-tetrahydro-5-quinolinecarboxylic acid
5-acetoxy-2-phenyl-5,6,7,8-tetrahydro-5-quinolinecarboxylic acid;
the sodium, potassium, lithium and ammonium salts of these acids;
the methyl esters, ethyl esters, propyl esters, isopropyl esters, butyl esters, tert.-butyl esters, pentyl esters, as well as hexyl esters of these acids; and
the dimethylamides, the diethylamides, the piperazides, as well as the morpholides of these acids;
furthermore the following:
2-phenyl-6,7-dihydro-5H-cyclopenta[b]pyridine-5-carboxylic acid
2-phenyl-3-chloro-6,7-dihydro-5H-cyclopenta[b]pyridine-5-carboxylic acid
2-(2-chlorophenyl)-6,7-dihydro-5H-cyclopenta[b]pyridine-5-carboxylic acid
2-(3-chlorophenyl)-6,7-dihydro-5H-cyclopenta[b]pyridine-5-carboxylic acid
2-(4-chlorophenyl)-6,7-dihydro-5H-cyclopenta[b]pyridine-5-carboxylic acid
2-(4-chlorophenyl)-3-chloro-6,7-dihydro-5H-cyclopenta[b]-pyridine-5-carboxylic acid
2-(2-fluorophenyl)-6,7-dihydro-5H-cyclopenta[b]pyridine-5-carboxylic acid
2-(3-fluorophenyl)-6,7-dihydro-5H-cyclopenta[b]pyridine-5-carboxylic acid
2-(4-fluorophenyl)-6,7-dihydro-5H-cyclopenta[b]pyridine-5-carboxylic acid
2-(4-fluorophenyl)-3-chloro-6,7-dihydro-5H-cyclopenta[b]pyridine-5-carboxylic acid
2-(3-bromophenyl)-6,7-dihydro-5H-cyclopenta[b]pyridine-5-carboxylic acid
2-(2,5-dichlorophenyl)-6,7-dihydro-5H-cyclopenta[b]pyridine-5-carboxylic acid
2-(3,4-dichlorophenyl)-6,7-dihydro-5H-cyclopenta[b]pyridine-5-carboxylic acid
2-(3,4-dichlorophenyl)-3-chloro-6,7-dihydro-5H-cyclopenta[b]pyridine-5-carboxylic acid
2-(2,4-dichlorophenyl)-6,7-dihydro-5H-cyclopenta[b]pyridine-5-carboxylic acid
2-(2-4-dichlorophenyl)-3-chloro-6,7-dihydro-5H-cyclopenta[b]pyridine-5-carboxylic acid
2-(2-trifluoromethylphenyl)-6,7-dihydro-5H-cyclopenta[b]pyridine-5-carboxylic acid
2-(3-trifluoromethylphenyl)-6,7-dihydro-5H-cyclopenta[b]pyridine-5-carboxylic acid
2-(4-trifluoromethylphenyl)-6,7-dihydro-5H-cyclopenta[b]pyridine-5-carboxylic acid
2-(4-trifluoromethylphenyl)-3-chloro-6,7-dihydro-5H-cyclopenta[b]pyridine-5-carboxylic acid
2-(3-tolyl)-6,7-dihydro-5H-cyclopenta[b]pyridine-5-carboxylic acid
2-(4-tolyl)-6,7-dihydro-5H-cyclopenta[b]pyridine-5-carboxylic acid
2-(3-chloro-4-tolyl)-6,7-dihydro-5H-cyclopenta[b]pyridine-5-carboxylic acid
2-(2-chloro-3-tolyl)-6,7-dihydro-5H-cyclopenta[b]pyridine-5-carboxylic acid
2-(3-chloro-2-tolyl)-6,7-dihydro-5H-cyclopenta[b]pyridine-5-carboxylic acid
2-(2-methoxyphenyl)-6,7-dihydro-5H-cyclopenta[b]pyridine-5-carboxylic acid
2-(3-methoxyphenyl)-6,7-dihydro-5H-cyclopenta[b]pyridine-5-carboxylic acid
2-(4-methoxyphenyl)-6,7-dihydro-5H-cyclopenta[b]pyridine-5-carboxylic acid
2-(4-methoxyphenyl)-3-chloro-6,7-dihydro-5H-cyclopenta[b]pyridine-5-carboxylic acid
2-(3,4-dimethoxyphenyl)-6,7-dihydro-5H-cyclopenta[b]pyridine-5-carboxylic acid
2-(3,4-dimethoxyphenyl)-3-chloro-6,7-dihydro-5H-cyclopenta[b]pyridine-5-carboxylic acid
2-(3,4-methylenedioxyphenyl)-6,7-dihydro-5H-cyclopenta[b]pyridine-5-carboxylic acid
2-(3,4-methylenedioxyphenyl)-3-chloro-6,7-dihydro-5H-cyclopenta[b]pyridine-5-carboxylic acid
2-cyclopentyl-6,7-dihydro-5H-cyclopenta[b]pyridine-5-carboxylic acid
5-acetoxy-2-phenyl-6,7-dihydro-5H-cyclopenta[b]pyridine-5-carboxylic acid;
the sodium, lithium, potassium and ammonium salts of these acids;
the methyl esters, ethyl esters, propyl esters, isopropyl esters, butyl esters, tert.-butyl esters, pentyl esters, as well as the hexyl esters of these acids; and
the dimethylamides, the diethylamides, the piperazides, and the morpholides of these acids.

Tetrazolyl derivatives of this invention

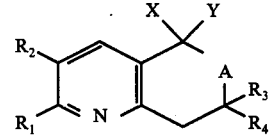

wherein $R_1$, $R_2$, Y, A, $R_3$ and $R_4$ are as above and X is 4-tetrazolyl, are obtained by treating a 5-cyanopyridine derivative

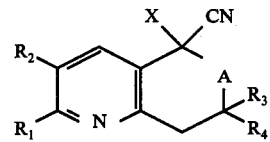

with an alkali metal azide in a polar aprotic solvent.

The nitriles can be reacted, for example, under the conventional conditions with an alkali metal azide, such as sodium azide, potassium azide or lithium azide, in polar aprotic solvents, such as dimethylformamide, N-methylacetamide, N-methylpyrrolidone, or hexamethylphosphoric triamide, to obtain the corresponding tetrazolyl compounds.

Pyridine-5-carboxylic acids of this invention (X is COOH in Formula I) are conveniently obtained by treating a tetrazolyl derivative (X is 4-tetrazolyl in Formula I) with a strong acid or strong base. That is, this conversion is conducted under the conditions customarily employed for the production of carboxylic acids from nitriles. Thus, it is possible, for example, to saponify the nitriles with strong bases, such as sodium hydroxide or potassium hydroxide, or also with strong acids, such as sulfuric acid, hydrochloric acid or perchloric acid. This reaction is suitably conducted by heating the nitriles in the presence of water, a solubilizer, such as methanol, ethanol, dimethylformamide, dioxane, or tetrahydrofuran, and the saponifying catalyst, such as the synthesis of pyridine-5-carboxylic acid, esters, salts, amides or hydroxamic acids is done by treating the pyridine-5-carboxylic acid (X is COOH in Formula I) with a esterification reagent, by treating the ester formed with a saponification reagent, by treating the acid or ester with an amidating or hydroxamating agent.

Thus, esters are made from the pyridine-5-carboxylic acids by conventional working methods. Thus, the acids can be reacted, for example, with diazomethane or diazoethane, to obtain the corresponding methyl or ethyl esters. Another generally applicable method is the reaction of the acids with the alcohols in the presence of carbonyl diimidazole or dicyclohexylcarbodiimide.

It is furthermore possible, for example, to react the acids in the presence of copper (I) oxide or silver oxide with alkyl halogenides.

A further method is conversion of the free acids to the corresponding acid alkyl esters using the corresponding dimethylformamide alkyl acetals. Moreover, the acids can be reacted with the alcohols or the lower-alkanecarboxylic acid esters of the alcohols in the presence of strongly acidic catalysts, such as hydrogen chloride, sulfuric acid, perchloric acid, trifluoromethylsulfonic acid, or p-toluenesulfonic acid.

It is also possible to convert the carboxylic acids into the acid chlorides or mixed acid anhydrides and to react the latter compounds with the alcohols in the presence of basic catalysts, such as pyridine, collidine, lutidine, or 4-dimethylaminopyridine.

Also, esters can be transesterified with the lastly desired alcohol in the presence of acidic or basic catalysts. In this connection, preferred acidic or basic catalysts are hydrogen chloride, sulfuric acid, phosphoric acid, p-toluenesulfonic acid, trifluoroacetic acid, and, for example, alkali alcoholates, alkaline earth alcoholates, or aluminum alcoholates.

Treatment of the ester formed with a saponification reagent to afford pyridine-5-carboxylate salts can be done, for example, by saponification of the ester in water or aqueous alcohols in the presence of acidic catalysts, including hydrochloric acid, sulfuric acid, p-toluenesulfonic acid, or in the presence of basic catalysts, including potassium bicarbonate, potassium carbonate, sodium hydroxide, or potassium hydroxide.

Salts of the carboxylic acids are also formed by neutralization of the acids by means of alkali metal carbonates, or alkali metal hydroxides, such as, for example, sodium carbonate, sodium bicarbonate, sodium hydroxide, potassium carbonate, potassium bicarbonate, or potassium hydroxide.

Amide formation or hydroxamic acid production from the free carboxylic acids or the reactive derivatives thereof is carried out according to the methods known for the purpose of amidating or hydroxamating acids. Thus, the carboxylic acids can be reacted, for example, under the conventional conditions with amines or hydroxylamine in the presence of dicyclohexylcarbodiimide, thus obtaining the corresponding aminocarbonyl compounds. It is also possible, for example, to convert the acid chlorides, mixed anhydrides, or esters corresponding to the carboxylic acids, under conventional conditions, to the corresponding amides or hydroxamic acids by treatment with ammonia, with amines, or with hydroxylamine.

A method for the synthesis of 5-hydroxy and 5-acyloxypyridines, compounds of Formula I in which Y is OH or acyloxy —$OCOR_7$, is metallating a compound of the formula

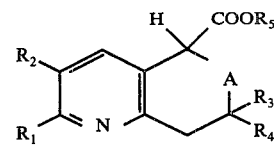

wherein $R_1$, $R_2$, $R_3$, $R_4$ and A are as above, with a proton-acceptor containing an alkali or alkaline earth metal in an aprotic solvent to produce a metallated intermediate III

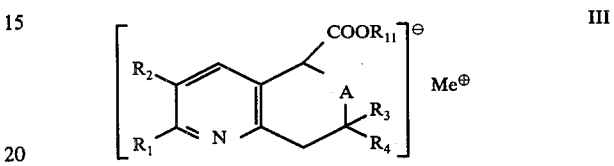

wherein $R_5$ is a $C_1$-$C_4$ alkyl and Me⊕ is an alkali metal cation which is oxidized with atmospheric oxygen to form a peroxide intermediate, which is reduced with a peroxide reducing agent and esterified if desired with a lower acid of 1-6 carbon atoms. The ester group can then, if desired, be saponified and transformed to a salt, a different ester, an amide, a hydroxamic acid or a nitrile group and the 5-hydroxy group can be esterified.

The starting compounds required for this aspect of this invention are conveniently prepared by reacting the nonmetallized carboxylic acids corresponding to the compounds in an aprotic solvent with a proton-acceptor containing an alkali metal or alkaline earth metal. Suitable aprotic solvents are, for example, polar ethers, such glycol dimethyl ether, tetrahydrofuran, or dioxane, or dipolar aprotic solvents, such as acetonitrile, dimethyl sulfoxide, N-methylpyrrolidone, hexamethylphosphoric triamide, or dimethylformamide. Suitable proton-acceptors include, for example, alkali amides, such as sodium amide or alkali or alkaline earth hydrides, such as sodium hydride, potassium hydride, calcium hydride, or lithium hydride, which is particularly preferred.

Atmospheric oxygen is introduced into the thus-prepared solution, and a resultant peroxide is optionally reduced with a reducing agent suitable for the reduction of peroxides, such as zinc, iron(II) sulfate, tin(II) chloride, sodium borohydride, lithium aluminum hydride, or triethyl phosphate. Triethylphosphate is especially preferred.

The preparation of compounds of the formula

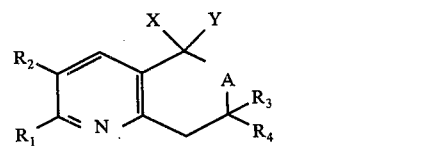

wherein Y is alkyl, carboxy or carbalkoxy and $R_1$, $R_2$, $R_3$, $R_4$, A, and X are as above by treating a compound of the formula

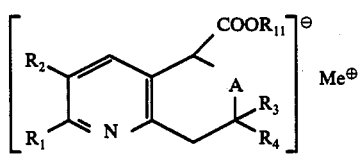

with an alkyl halogenide or with a chlorocarbonic acid ester and, if desired, converting the product to form a free acid, a salt, another ester, an amide, a hydroxamic acid or a nitrile.

This aspect of the invention is preferably accomplished by producing solutions of compounds of general Formula III in the above-described manner and reacting same with alkyl halogenides, of the formula $R_9$-halogenide, preferably chlorides, bromides, or iodides, or with chlorocarbonic acid esters, of the formula Cl $COOR_{10}$.

5-Amino- or 5-acylaminopyridine compounds of the formula

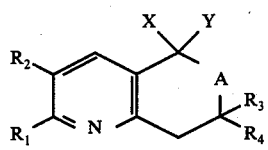

wherein $R_1$, $R_2$, $R_3$, $R_4$ and A are as above; Y is $NH_2$ or alkanoylamino, and X is —CN, or a carboxylic acid derivative are obtained by hydrolyzing a hydantoin precursor of the formula

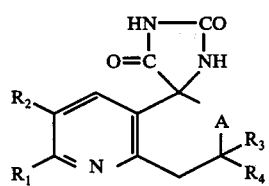

with a strong acid or strong base to produce an amino acid of the formula

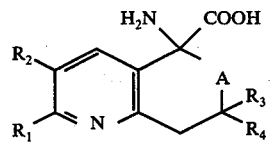

of which the amino group can be acylated to produce an acylamino compound and the acid group can be converted to a salt, ester, amide, hydroxamic acid or nitrile group.

The process according to the invention is conducted under the conditions usually employed for the hydrolysis of hydantoins with strong acids, such as sulfuric acid, hydrogen chloride, or hydrogen iodide, or with strong acids, such as sodium hydroxide or potassium hydroxide, preferably in aqueous solution under reflux.

Derivatives of pyridines with an amino-, an acylamino-, a hydroxyl-, or an acyloxy-substituent at the 5-position and corresponding to the formula

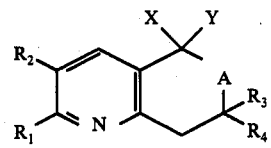

wherein $R_1$, $R_2$, $R_3$, $R_4$, A and X are as above, and Y is OH, acyloxy, $NH_2$ or acylamino, as above, are prepared from a compound of the formula

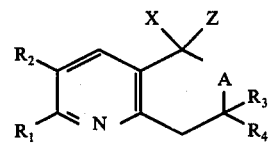

wherein $R_1$, $R_2$, $R_3$, $R_4$, X and A are as above and Z is Cl, Br or I and a compound of the formula MOH or MOCOR or a reagent for the Perkin synthesis or Gabriel synthesis, where M is an alkali metal cation.

This aspect of the invention is achieved under the conditions customarily used for exchanging halogen atoms for the aforementioned groups.

Thus, it is possible, for example, to react the compounds of general Formula V with alkali metal hydroxide solutions, thus obtaining the hydroxy compounds. Furthermore, the compounds of Formula V can be reacted with alkali salts of carboxylic acids, thus producing the alkanoyloxy compounds of general Formula I (X is $-OCOR_7$).

The amino compounds of general Formula I can be prepared from the compounds of Formula V, for example, with the aid of the Perkin synthesis or the Gabriel synthesis. The Perkin-synthesis may be conducted by treating the compounds of Formula V with an excess of concentrated aqueous ammonia solution at 0° C to 80° C. The Gabriel synthesis may be conducted by treating the compounds of Formula V with potassium phthalimide in a polar solvent such as dimethyl sulfoxide, tetrahydrofuran or dimethylformamide and hydrolysing the resulting product with mineral acids such as hydrochloric acid.

The preparation of 5-cyanopyridine derivatives of the formula

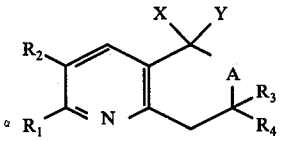

wherein X is CN is accomplished by treating a 5-halopyridine compound of the formula

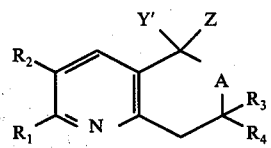

where $R_1$, $R_2$, $R_3$, $R_4$ and A are as above and Z is Cl, Br or I with an alkali metal cyanide in a polar solvent at a temperature from 0° to about 160° C.

The nitriles of general Formula I can be prepared from compounds of general Formula VI, for example, by reacting same with alkali cyanides. Solvents which can be used include dipolar aprotic solvents such as dimethyl sulfoxide, dimethyl formamide or hexamethyl phosphoric acid triamide. Preferably, the reaction is done at a temperature between about 20° and about 50° C.

The optionally following conversion of reactive derivatives of carboxylic acids into nitriles likewise takes place in accordance with the operating methods known therefore, e.g. by treating the corresponding aminocarbonyl compounds, under the conventional conditions, with dehydrating agents, such as, e.g. dicyclohexylcarbodiimide, carbonyl diimidazole, polyphosphoric acid, thionyl chloride, or phosphorus oxychloride. Preferred conditions are:

The acylation of free hydroxy groups or free amino groups, which follows as an optional measure, also takes place with the aid of known operating methods. An example is the acylation with the aid of acid chlorides or acid anhydrides, optionally with the use of basic catalysts, such as sodium carbonate, sodium bicarbonate, potassium bicarbonate, sodium hydroxide, potassium hydroxide, pyridine, lutidine, or collidine.

The novel pyridine derivatives of general Formula I are pharmacologically active substances which are distinguished, in particular, by a pronounced anti-inflammatory effectiveness and an only relatively minor toxicity. Moreover, these compounds are often distinguished by a rapid onset of effectiveness, a high intensity of effectiveness, and a long duration of activity; they exhibit a favorable resorbability and, in galenic preparations, a relatively good stability.

The pyridine derivatives of general Formula I are metabolized in the body in a different way than the known anti-inflammatory compounds.

The compounds are suitable, in combination with the vehicles customary in galenic pharmacy, for the treatment of, for example:

(a) local: contact dermatitis, exzema of a great variety of types, neurodermitis, erythrodermia, first degree burns, pruritus vulvae et ani, rosacea, erythematodes cutaneus, psoriasis, lichen ruber planus et verrucosus;

(b) oral: acute and chronic polyarthritis, neurodermitis, asthma bronchiale, hay fever, etc.

The special drug preparations are produced in the usual manner by converting the effective agents with suitable additives, carrier substances, and flavor-ameliorating agents into the desired forms of application, such as tablets, dragees, capsules, solutions, ointments, inhalants, etc.

The compounds of this invention can be employed in mixture with conventional excipients, i.e., pharmacologically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixier or the like can be used wherein a sweetened vehicle is employed. Sustained release compositions can be formulated including those wherein the active compound is protected with differentially degradable coatings, e.g. by microencapsulation, multiple coatings, etc.

Generally, the compounds of this invention are dispensed in unit dosage form comprising 0–500 mg. of a pharmaceutical carrier per each unit dosage and the amount of active agent of the invention per unit dosage is about 50 to 500 mg.

For topical application, these are employed as nonsprayable forms, viscous to semi-solid or solid forms comprising a carrier indigenous to topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers, or salts for influencing osmotic pressure, etc. For topical application, also suitable are a sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The compounds of this invention are generally administered to animals, including but not limited to mammals, e.g., and humans. An anti-inflammatory effective daily dosage of the active compounds as administered orally to humans generally comprises about 50 to 500, preferably 100 to 250 mg together with 0, - 500 mg. of pharmaceutically acceptable carrier. The dose can be administered singly or as divided dosages throughout the day.

Especially suitable for oral administration are tablets, dragees, and capsules, containing for example, 1-250 mg. of active agent and 50 mg. to 2 g. of a pharmacologically inactive carrier, such as, for example, lactose, amylose, talc, gelatin, magnesium stearate, and similar agents, as well as the customary additives. Suitable for topical application are powders, ointments, aerosols, and similar preparations containing preferably 0.01 - 2% of the active agent.

Oral administration is preferred, the compounds of this invention being particularly valuable in the treatment of humans afflicted with polyarthritis. In this regard, they can be employed in substantially the same manner as the known compounds.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

The starting compounds of general Formulae II–VIII for the process of this invention are produced in accordance with methods generally known to a person skilled in the art and which will be explained in the following examples with reference to typical representatives.

The examples set forth below serve to further explain the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

13 g. of 1-phenyl-2-propyn-1-one and 11 g. of 1-amino-1-cyclohexen-3-one are dissolved in 100 ml. of dimethylformamide, agitated for 2 hours at room temperature and for 2 hours at 150° C. and then evaporated under vacuum to dryness. The reaction mixture is recrystallized from ethanol, thus obtaining 2-phenyl-5,6,7,8-tetrahydro-5-quinolone, m.p. 130°–131° C.

Analogously, the following compounds can be prepared:
(a) from 4.1 g. of 1-cyclohexyl-2-propyn-1-one and 3.3 g. 1-amino-1-cyclohexen-3-one: 2-cyclohexyl-5,6,7,8-tetrahydro-5-quinolone (oil);
(b) from 14.4 g. of 1-(2-tolyl)-2-propyn-1-one and 11 g. of 1-amino-1-cyclohexen-3-one: 2-(2-tolyl)-5,6,7,8-tetrahydro-5-quinolone, m.p. 115.5° C. (ethanol);
(c) from 3.3 g. of 1-(4-chlorophenyl)-2-propyn-1-one and 2.2 g. of 1-amino-1-cyclohexen-3-one: 2-(4-chlorophenyl)-5,6,7,8-tetrahydro-5-quinolone, m.p. 118° – 118.5° C. (ethanol);
(d) from 3.2 g. of 1-(4-methoxyphenyl)-2-propyn-1-one and 2.2 g. of 1-amino-1-cyclohexen-3-one: 2-(4-methoxyphenyl)-5,6,7,8-tetrahydro-5-quinolone, m.p. 116° –117° C.;
(e) from 13 g. of 1-phenyl-2-propyn-1-one and 14 g. of 1-amino-5,5-dimethyl-1-cyclohexen-3-one: 7,7-dimethyl-2-phenyl-5,6,7,8-tetrahydro-5-quinolone, m.p. 72.5° C. (hexane);
(f) from 11 g. of 5-methyl-1-hexyn-3-one and 12 g. of 1-amino-1-cyclohexen-3-one: 2-isobutyl-5,6,7,8-tetrahydro-5-quinolone (oil).

EXAMPLE 2

18.7 g. of 2-phenyl-5,6,7,8-tetrahydro-5-quinolone is dissolved in 100 ml. of absolute benzene and 50 ml. of absolute ether and, within 20 minutes, added dropwise to 3.2 g. of lithium aluminum hydride/50 ml. of absolute ether. The mixture is agitated for 1 hour, combined with water under ice cooling, the ether phase is concentrated, and the reaction mixture is recrystallized from diisopropyl ether, thus obtaining 2-phenyl-5,6,7,8-tetrahydro-5-quinolinol, m.p. 94°–95° C.

Analogously, the following compounds can be prepared:
(a) 2-cyclohexyl-5,6,7,8-tetrahydro-5-quinolinol, m.p. 80°–81° C. (hexane);
(b) 2-(2-tolyl)-5,6,7,8-tetrahydro-5-quinolinol, m.p. 131°–132° C. (diisopropyl ether);
(c) 2-(4-chlorophenyl)-5,6,7,8-tetrahydro-5-quinolinol, m.p. 128° – 129° C. (diisopropyl ether);
(d) 2-(4-methoxyphenyl)-5,6,7,8-tetrahydro-5-quinolinol, m.p. 101° – 103° C.
(e) 7,7-dimethyl-2-phenyl-5,6,7,8-tetrahydro-5-quinolinol, m.p. 103° C. (diisopropyl ether);
(f) 2-isobutyl-5,6,7,8-tetrahydro-5-quinolinol, m.p. 75.5° – 76° C. (diisopropyl ether);
(g) 2-phenyl-6,7-dihydro-5H-cyclopenta[b]pyridin-5-ol, m.p. 114°–115° C.

EXAMPLE 3

16.9 g. of 2-phenyl-5,6,7,8-tetrahydro-5-quinol in 300 ml. of absolute chloroform and 7.2 ml. of thionyl chloride are heated for 1 hour to 60° C. and extracted three times with saturated sodium bicarbonate solution. The chloroform phase is concentrated, the residue is crystallized from hexane; the product is 5-chloro-2-phenyl-5,6,7,8-tetrahydroquinoline, m.p. 88°–89° C.

Analogously, the following compounds can be prepared:
(a) 5-chloro-2-cyclohexyl-5,6,7,8-tetrahydroquinoline, hydrochloride, m.p. 183°–185° C. (chloroform);
(b) 5-chloro-(2-tolyl)-5,6,7,8-tetrahydroquinoline, m.p. 37°–38° C. (pentane);
(c) 5-chloro-2-(4-chlorophenyl)-5,6,7,8-tetrahydroquinoline, m.p. 94.5° – 95° C. (hexane);
(d) 5-chloro-2-(4-methoxyphenyl)-5,6,7,8-tetrahydroquinoline, m.p. 76.5° – 77° C.
(e) 5-chloro-7,7-dimethyl-2-phenyl-5,6,7,8-tetrahydroquinoline (oil);
(f) 5-chloro-2-isobutyl-5,6,7,8-tetrahydroquinoline, m.p. 50.5° – 51.5° C. (hexane);
(g) 5-chloro-2-phenyl-6,7-dihydro-5H-cyclopenta[b]pyridine, m.p. 73° – 73.5° C.

EXAMPLE 4

12 g. of 5-chloro-2-phenyl-5,6,7,8-tetrahydroquinoline and 10 g. of sodium cyanide are dissolved in 200 ml. of absolute dimethyl sulfoxide. After 48 hours, the mixture, under vacuum, is evaporated to dryness, the oily residue is taken up in ethyl acetate, extrated three times with water, and the ethyl acetate is concentrated, thus obtaining 2-phenyl-5,6,7,8-tetrahydro-5-quinoline carbonitrile, m.p. 98°–99° C. (ethyl acetate/hexane).

Analogously, the following compounds can be prepared:
(a) 2-cyclohexyl-5,6,7,8-tetrahydro-5-quinoline carbonitrile (oil);
(b) 2-(2-tolyl)-5,6,7,8-tetrahydro-5-quinoline carbonitrile, m.p. 78°–80° C. (hexane);
(c) 2-(4-chlorophenyl)-5,6,7,8-tetrahydro-5-quinoline carbonitrile, m.p. 93°–95° C. (hexane);
(d) 2-(4-methoxyphenyl)-5,6,7,8-tetrahydro-5-quinoline carbonitrile, m.p. 78.5° – 79.5° C.
(e) 7,7-dimethyl-2-phenyl-5,6,7,8-tetrahydro-5-quinoline carbonitrile (oil);
(f) 2-isobutyl-5,6,7,8-tetrahydro-5-quinoline carbonitrile (oil);
(g) 2-phenyl-6,7-dihydro-5H-cyclopenta[b]pyridine-5-carbonitrile, m.p. 119°–120° C.;
(h) 3-chloro-2-cyclohexyl-5,6,7,8-tetrahydro-5-quinoline carbonitrile (oil).

EXAMPLE 5

3.3 g. of 2-phenyl-5,6,7,8-tetrahydroquinoline-5-carbonitrile is dissolved in 100 ml. of ethanolic hydrochloric acid and heated for 6 hours to 80° C. The reaction mixture is concentrated and taken up in ethyl acetate, then extracted three times with saturated sodium bicarbonate solution, and the ethyl acetate is distilled off, thus obtaining the ethyl ester of 2-phenyl-5,6,7,8-tetrahydro-5-quinolinecarboxylic acid (oil).

Analogously, the following compounds can be prepared by refluxing with methanolic hydrochloric acid:
(a) the methyl ester of 2-phenyl-5,6,7,8-tetrahydro-5-quinolinecarboxylic acid (oil);
(b) the ethyl ester of 2-cyclohexyl-5,6,7,8-tetrahydro-5-quinolinecarboxylic acid (oil);
(c) the ethyl ester of 2-(2-tolyl)-5,6,7,8-tetrahydro-5-quinolinecarboxylic acid (oil);
(d) the ethyl ester of 2-(4-chlorophenyl)-5,6,7,8-tetrahydro-5-quinolinecarboxylic acid (oil);
(e) the ethyl ester of 2-(4-methoxyphenyl)-5,6,7,8-tetrahydro-5-quinolinecarboxylic acid (oil);
(f) the ethyl ester of 7,7-dimethyl-2-phenyl-5,6,7,8-tetrahydro-5-quinolinecarboxylic acid (oil);
(g) the ethyl ester of 2-isobutyl-5,6,7,8-tetrahydro-5-quinolinecarboxylic acid (oil);
(h) the ethyl ester of 2-phenyl-6,7-dihydro-5H-cyclopenta[b]pyridine-5-carboxylic acid (oil);
(i) the ethyl ester of 3-chloro-2-cyclohexyl-5,6,7,8-tetrahydro-5-quinolinecarboxylic acid (oil);
(j) the ethyl ester of 5-methyl-2-phenyl-5,6,7,8-tetrahydro-5-quinolinecarboxylic acid (oil).

EXAMPLE 6

3.3 g. of 2-phenyl-5,6,7,8-tetrahydro-5-quinolinecarboxylic acid ethyl ester is dissolved in 80 ml. of ethanol and 27 ml. of 2N sodium hydroxide solution. After 3 hours, the reaction mixture is concentrated, the oily residue is distributed between ether/water, and the aqueous phase is adjusted to pH 5 with 2N hydrochloric acid. The reaction mixture is vacuum filtered and recrystallized from methanol, thus obtaining 2-phenyl-5,6,7,8-tetrahydro-5-quinolinecarboxylic acid, m.p. 215° C.

Analogously, the following compounds can be prepared:
(a) 2-cyclohexyl-5,6,7,8-tetrahydro-5-quinolinecarboxylic acid, m.p. 201°–202° C.;
(b) 2-(2-tolyl)-5,6,7,8-tetrahydro-5-quinolinecarboxylic acid, m.p. 167° C.;
(c) 2-(4-chlorophenyl)-5,6,7,8-tetrahydro-5-quinolinecarboxylic acid, m.p. 216.5° C.;
(d) 2-(4-methoxyphenyl)-5,6,7,8-tetrahydro-5-quinolinecarboxylic acid; m.p. 166° – 167° C.
(e) 7,7-dimethyl-2-phenyl-5,6,7,8-tetrahydro-5-quinolinecarboxylic acid, m.p. 191° C.;
(f) 2-isobutyl-5,6,7,8-tetrahydro-5-quinolinecarboxylic acid; m.p. 93°–94° C.
(g) 2-phenyl-5,6-dihydro-5H-cyclopenta[b]pyridine-5-carboxylic acid, m.p. 222°–224° C.;
(h) 3-chloro-2-cyclohexyl-5,6,7,8-tetrahydro-5-quinolinecarboxylic acid, m.p. 178°–179° C.
(i) 5-methyl-2-phenyl-5,6,7,8-tetrahydro-5-quinolinecarboxylic acid; m.p. 210°–211° C.
(j) 2-(4-isopropylphenyl)-5,6,7,8-tetrahydro-5-quinoline-carboxylic acid, m.p. 169°–170.5° C.
(k) 2-(2-methylpropyl)-5,6,7,8-tetrahydro-5-quinoline-carboxylic acid, m.p. 121°–122° C.
(l) 2-(4-fluorophenyl)-5,6,7,8-tetrahydro-5-quinoline-carboxylic acid, m.p. 219°–221° C.
(m) 2-(2,5-dimethylphenyl)-5,6,7,8-tetrahydro-5-quinoline-carboxylic acid, m.p. 193°–194° C.
(n) 2-(2-chlorophenyl)-5,6,7,8-tetrahydro-5-quinoline-carboxylic acid, m.p. 186°–190° C.
(o) 2-cyclohexyl)-6,7-dihydro-5[H]-cyclopentapyridine-5-carboxylic acid, m.p. 150°–151° C.

EXAMPLE 7

2.8 g. of the ethyl ester of 2-phenyl-5,6,7,8-tetrahydro-5-quinolinecarboxylic acid is dissolved in 30 ml. of absolute dimethylformamide; dry oxygen is conducted for 1 hour through the solution at 0° C., the solution is concentrated, neutralized with acetic acid, and distributed between ethyl acetate/water. The ethyl acetate phase is concentrated, and the oily residue is dissolved in 40 ml. of methanol and 20 ml. of 2N sodium hydroxide solution. After 3 hours, the mixture is concentrated, combined with water/ether, and the alkaline phase is adjusted to pH 5 with hydrochloric acid, thus obtaining 5-hydroxy-2-phenyl-5,6,7,8-tetrahydro-5-quinolinecarboxylic acid, m.p. 204.5° C. (water).

EXAMPLE 8

Two grams of 5-hydroxy-2-phenyl-5,6,7,8-tetrahydro-5-quinolinecarboxylic acid is agitated for 1 hour with 20 ml. acetic anhydride; concentrated; and the oily residue crystallized after 5 hours of agitation with water, thus obtaining 5-acetoxy-2-phenyl-5,6,7,8-tetrahydro-5-quinolinecarboxylic acid, m.p. 185° C.

EXAMPLE 9

2.7 g. of 5-amino-2-phenyl-5,6,7,8-tetrahydro-5-quinolinecarboxylic acid (Example 14) is dissolved in 50 ml. of dimethylformamide, combined with 1 ml. of acetic anhydride, stirred for 1 hour at 0° C., concentrated, and recrystallized from water, thus obtaining 5-acetamido-2-phenyl-5,6,7,8-tetrahydro-5-quinolinecarboxylic acid, m.p. 213° C.

EXAMPLE 10

Five grams of the ethyl ester of 2-phenyl-5,6,7,8-tetrahydro-5-quinolinecarboxylic acid is heated in 50 ml. of alcoholic ammonia for 2 hours to 60° C., then concentrated and crystallized from ethyl acetate, thus obtaining 2-phenyl-5,6,7,8-tetrahydro-5-quinolinecarboxylic acid amide, m.p. 132° C.

EXAMPLE 11

2.8 g. of the ethyl ester of 2-phenyl-5,6,7,8-tetrahydro-5-quinolinecarboxylic acid is dissolved in 80 ml. of absolute ethanol and heated for 2 hours to 80° C. with 4.1 g. of sodium ethylate and 3.5 g. of hydroxylamine hydrochloride. The reaction mixture is concentrated, the oily residue is distributed between ether/water, and the aqueous phase is adjusted to pH 5 with 2N hydrochloric acid, thus obtaining 2-phenyl-5,6,7,8-tetrahydro-5-quinoline-hydroxamic acid, m.p. 167°–168° C. (diisopropyl ether).

EXAMPLE 12

2.3 g. of 2-phenyl-5,6,7,8-tetrahydro-5-quinoline carbonitrile and 2.6 g. of sodium azide are dissolved in 30 ml. of dimethylformamide and 2.4 ml. of acetic acid and heated for 16 hours to 100° C. The mixture is concentrated under vacuum, distributed between ethyl acetate/water, and the ethyl acetate phase is extracted twice with 1N sodium hydroxide solution. The alkaline phase is set to pH 5 with hydrochloric acid and extracted three times with ethyl acetate. The reaction mixture is recrystallized from ethyl acetate/diisopropyl ether, thus producing 5-(2-phenyl-5,6,7,8-tetrahydro-5-quinolyl), m.p. 195° C.

EXAMPLE 13

4.5 g. of 2-phenyl-5,6,7,8-tetrahydro-5-quinolone, 11.1 g. of ammonium carbonate, 2 g. of sodium cyanide in 200 ml. of methanol and 100 ml. of water are heated for 24 hours to 60° C., then vacuum-filtered, and the crystallized product is washed thoroughly with water, thus obtaining 2',4'-dioxo-2-phenyl-1',2',3',7,8-hexahydro-spiro[quinoline-5,6H,5'-imidazole], m.p. 311°–314° C.

EXAMPLE 14

2.9 g. of 2',4'-dioxo-2-phenyl-1',2',3',7,8-hexahydrospiro[quinoline-5,6H,5'-imidazole] in 50 ml. of 2N sodium hydroxide solution is heated for 72 hours to 110° C., then vacuum-filtered, and set to pH 7 with hydrochloric acid, thus obtaining 5-amino-2-phenyl-5,6,7,8-tetrahydro-5-quinolinecarboxylic acid, m.p. 263° C. (water).

EXAMPLE 15

860 mg. of 5-chloro-2-cyclohexyl-5,6,7,8-tetrahydroquinoline is dissolved in 20 ml. of acetonitrile; 1.1 g. of chlorine gas is introduced into the reaction mixture, and the latter is combined with 1 g. of anhydrous aluminum chloride. After 5 hours at 60° C., the mixture is concentrated, taken up in ethyl acetate, extracted three times with saturated sodium bicarbonate solution, and the ethyl acetate is distilled off under vacuum, thus obtaining 3,5-dichloro-2-cyclohexyl-5,6,7,8-tetrahydroquinoline in the form of an oil.

EXAMPLE 16

2.1 ml. of absolute diisopropylamine in 30 ml. of absolute tetrahydrofuran is combined under a nitrogen atmosphere at −15° C. with 6 ml. of 2-molar butyllithium solution, then left for 10 minutes at this temperature, and thereafter 2.8 g. of the ethyl ester of 2-phenyl-5,6,7,8-tetrahydro-5-quinoline-carboxylic acid in 50 ml. of tetrahydrofuran is added dropwise thereto within 15 minutes. After 30 minutes at −5° C., dry carbonic acid is introduced for 30 minutes. The reaction mixture is concentrated, distributed between ether/1N sodium hydroxide solution, and the alkaline phase is adjusted to pH 5 with 2N hydrochloric acid, thus obtaining 5-methoxycarbonyl-2-phenyl-5,6,7,8-tetrahydro-5-quinolinecarboxylic acid diisopropylamide, m.p. 183° C. (methanol).

EXAMPLE 17

12 g. of the ethyl ester of 2-methyl-6-phenyl-3-pyridinecarboxylic acid, 9 g. of N-bromosuccinimide, 1 g. of benzoyl peroxide in 250 ml. of carbon tetrachloride are refluxed for 1½ hours under UV irradiation. The reaction mixture is then vacuum-filtered, the solvent is distilled off; the residue is taken up in 20 ml. of absolute dimethylformamide and added dropwise within 20 minutes to a solution of 11.8 g. of the diethyl ester of sodium-malonic acid in 50 ml. of absolute dimethylformamide. After 24 hours, the reaction mixture is concentrated, dissolved in ethyl acetate, extracted three times with saturated sodium bicarbonate solution, and recrystallized from ethanol, thus obtaining the ethyl ester of (3-ethoxycarbonyl-6-phenyl-2-pyridyl)-malonic acid, m.p. 125°–126° C.

EXAMPLE 18

8.8 g. of the diethyl ester of (3-ethoxycarbonyl-6-phenyl-2-pyridyl)-malonic acid in 300 ml. of absolute tetrahydrofuran is introduced dropwise within 2 hours at 70° C. into a solution of 1.4 g. of sodium hydride, 80% strength, in 40 ml. of absolute tetrahydrofuran; the reaction mixture is stirred for 1 hour at 70° C. and then concentrated. The residue is distributed between ether/water, the aqueous phase is set to pH 5 with 2N hydrochloric acid and extracted three times with chloroform. The chloroform phase is concentrated and recrystallized from diisopropyl ether, thus obtaining the ethyl ester of 5-oxo-2-phenyl-6,7-dihydro-5H-cyclopenta[b]pyridine-6-carboxylic acid, m.p. 85°–86° C.

EXAMPLE 19

2.5 g. of the ethyl ester of 5-oxo-2-phenyl-6,7-dihydro-5H-cyclopenta[b]pyridine-6-carboxylic acid is heated with 250 ml. of 2N sulfuric acid for 45 minutes to 110° C., extracted once with ether, and neutralized with soda. After extraction with ethyl acetate and recrystallization from ethanol, 2-phenyl-6,7-dihydro-5H-cyclopenta[b]pyridin-5-one is obtained, m.p. 177°–178° C.

EXAMPLE 20

4.7 g. of 2-phenyl-5,6,7,8-tetrahydro-5-quinoline carbonitrile in 80 ml. of absolute tetrahydrofuran is combined with 0.660 g. of 80% sodium hydride, agitated for 30 minutes at room temperature and for 30 minutes at 60° C. under nitrogen, and combined with 2.5 ml. of methyl iodide. After heating the mixture for 2 hours to 60° C., it is concentrated, distributed between ethyl acetate/water, and the ethyl acetate phase is concentrated. Recrystallization from diisopropyl ether/hexane yields 5-methyl-2-phenyl-5,6,7,8-tetrahydro-5-quinoline carbonitrile, m.p. 114.5° – 115.5° C.

The preceding examples can be repeated with similar success by substituting the generically and specifically desecribed reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound selected from the group consisting of 2-phenyl-5,6,7,8-tetrahydro-5-quinoline carbonitrile, 2-phenyl-5,6,7,8-tetrahydro-5-quinolinehydroxamic acid, 5-hydroxy-2-phenyl-5,6,7,8-tetrahydro-5-quinoline-carboxylic acid, 5-acetoxy-2-phenyl-5,6,7,8tetrahydro-5-quinoline-carboxylic acid, 5-amino-2-phenyl-5,6,7,8-tetrahydro-5-quinoline-carboxylic acid, 5-acetamino-2-phenyl-5,6,7,8-tetrahydro-5-quinoline-carboxylic acid, -5-methyl-2-phenyl-,5,6,7,8-tetrahydro-5-quinoline-carboxylic acid, 7,7-dimethyl-2-phenyl-,5,6,7,8-tetrahydro-5-quinoline carbonitrile, 7,7-dimethyl-2-phenyl-5,6,7,8-tetrahydro-5-quinolinecarboxylic acid, 2-(4-chlorophenyl)-5,6,7,8-tetrahydro-5-quinoline carbonitrile, 2-(4-chlorophenyl)-5,6,7,8-tetrahydro-5-quinolinecarboxylic acid, 2-(2-tolyl)-5,6,7,8-tetrahydro-5-quinoline-carbonitrile, 2-(2-tolyl)-5,6,7,8-tetrahydro-5-quinoline-carboxylic acid, 2-(4-methoxyphenyl-5,6,7,8-tetrahydro-5-quinoline carbonitrile, 2-(4-methoxyphenyl)- 5,6,7,8-tetrahydro- 5-quinolinecarboxylic acid, 2-cyclohexyl-5,6,7,8-tetrahydro-5-quinoline carbonitrile, 2-cyclohexyl-5,6,7,8-tetrahydro-5-quinoline carboxylic acid, 2-isobutyl-5,6,7,8-tetrahydro-5-quinoline carbonitrile, 2-isobutyl-5,6,7,8-tetrahydro-5-quinoline carboxylic acid, 3-chloro-2-cyclohexyl5,6,7,8-tetrahydro-5-quinoline carbonitrile, and 3-chloro-2-cyclohexyl-5,6,7,8-tetrahydro-5-quinolinecarboxylic acid.

2. A tetrahydroquinoline of the formula

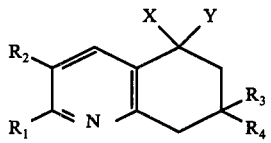

wherein $R_1$ is phenyl; $R_2$, $R_3$ and $R_4$ each are H; X is COOH and Y is OH, alkanoyloxy of 1-10 carbon atoms, $NH_2$, alkanoylamino of 1-6 carbon atoms or alkyl of 1-10 carbon atoms.

3. A tetrahydroquinoline of the formula

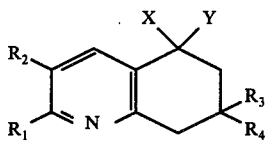

wherein $R_1$ is alkyl of 1-10 carbon atoms, phenyl or phenyl substituted by 1-2 halogen, alkoxy or alkyl of 1-4 carbon atoms or methylenedioxy; $R_2$ is H or Cl; $R_3$, $R_4$ and Y each are H; and X is cyano.

4. 2-Phenyl-5,6,7,8-tetrahydro-5-quinoline carbonitrile, a compound of claim 1.

5. 2-Phenyl-5,6,7,8-tetrahydro-5-quinolinehydroxamic acid, a compound of claim 1.

6. 5-Hydroxy-2-phenyl-5,6,7,8-tetrahydro-5-quinolinecarboxylic acid, a compound of claim 1.

7. 5-Acetoxy-2-phenyl-5,6,7,8-tetrahydro-5-quinolinecarboxylic acid, a compound of claim 1.

8. 5-Amino-2-phenyl-5,6,7,8-tetrahydro-5-quinolinecarboxylic acid, a compound of claim 1.

9. 5Acetamino-2-phenyl-5,6,7,8-tetrahydro-5-quinolinecarboxylic acid, a compound of claim 1.

10. 5-Methyl-2-phenyl-5,6,7,8-tetrahydro-5-quinolinecarboxylic acid, a compound of claim 1.

11. 7,7-Dimethyl-2-phenyl-5,6,7,8-tetrahydro-5-quinoline carbonitrile, a compound of claim 1.

12. 7,7-Dimethyl-2-phenyl-5,6,7,8-tetrahydro-5-quinolinecarboxylic acid, a compound of claim 1.

13. 2-(4-Chlorophenyl)-5,6,7,8-tetrahydro-5-quinoline carbonitrile, a compound of claim 1.

14. 2-(4-Chlorophenyl)-5,6,7,8-tetrahydro-5-quinolinecarboxylic acid, a compound of claim 1.

15. 2-(2-Tolyl)-5,6,7,8-tetrahydro-5-quinoline-carbonitrile, a compound of claim 1.

16. 2-(2-Tolyl)-5,6,7,8-tetrahydro-5-quinolinecarboxylic acid, a compound of claim 1.

17. 2-(4-Methoxyphenyl)-5,6,7,8-tetrahydro-5-quinoline carbonitrile, a compound of claim 1.

18. 2-(4-Methoxyphenyl)-5,6,7,8-tetrahydro-5-quinolinecarboxylic acid, a compound of claim 1.

19. 2-Cyclohexyl-5,6,7,8-tetrahydro-5-quinoline carbonitrile, a compound of claim 1.

20. 2-Cyclohexyl-5,6,7,8-tetrahydro-5-quinolinecarboxylic acid, a compound of claim 1.

21. 2-Isobutyl-5,6,7,8-tetrahydro-5-quinoline carbonitrile, a compound of claim 1.

22. 2-Isobutyl-5,6,7,8-tetrahydro-5-quinolinecarboxylic acid, a compound of claim 1.

23. 3-Chloro-2-cyclohexyl-5,6,7,8-tetrahydro-5-quinoline carbonitrile, a compound of claim 1.

24. 3-Chloro-2-cyclohexyl-5,6,7,8-tetrahydro-5-quinolinecarboxylic acid, a compound of claim 1.

25. A pharmaceutical composition comprising in unit dosage form an anti-inflammatorily effective amount of a compound of claim 1 in admixture with a pharmaceutically acceptable carrier.

26. A method for the treatment of inflammation comprising administration to the affected patient an anti-inflammatorily effective amount of a compound of claim 1.

27. 2-(4-isopropylphenyl)-5,6,7,8-tetrahydro-5-quinolinecarboxylic acid, a compound of claim 1.

28. 2-(2-methylpropyl)-5,6,7,8-tetrahydro-5-quinolinecarboxylic acid, a compound of claim 1.

29. 2-(4-fluorophenyl)-5,6,7,8-tetrahydro-5-quinolinecarboxylic acid, a compound of claim 1.

30. 2-(2,5-dimethylphenyl)-5,6,7,8-tetrahydro-5-quinolinecarboxylic acid, a compound of claim 1.

31. 2-(2-chlorophenyl)-5,6,7,8-tetrahydro-5-quinolinecarboxylic acid, a compound of claim 1.

* * * * *